United States Patent
Brannan et al.

(10) Patent No.: US 9,277,969 B2
(45) Date of Patent: Mar. 8, 2016

(54) MICROWAVE ABLATION SYSTEM WITH USER-CONTROLLED ABLATION SIZE AND METHOD OF USE

(75) Inventors: Joseph D. Brannan, Erie, CO (US); Kyle R. Rick, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1896 days.

(21) Appl. No.: 12/416,583

(22) Filed: Apr. 1, 2009

(65) Prior Publication Data
US 2010/0256624 A1    Oct. 7, 2010

(51) Int. Cl.
*A61B 19/00* (2006.01)
*A61B 18/18* (2006.01)

(52) U.S. Cl.
CPC ................. *A61B 19/50* (2013.01); *A61B 18/18* (2013.01); *A61B 18/1815* (2013.01); *A61B 2019/501* (2013.01); *A61B 2019/504* (2013.01); *A61B 2019/507* (2013.01)

(58) Field of Classification Search
CPC .... A61B 18/18; A61B 18/1815; A61B 19/50; A61B 2019/501; A61B 2019/504; A61B 2019/507
USPC ............ 606/33; 600/471, 300, 407, 463, 411, 600/416
See application file for complete search history.

(56) References Cited

U.S. PATENT DOCUMENTS

| | | |
|---|---|---|
| 3,631,363 A | 12/1971 | Miller |
| 4,397,313 A | 8/1983 | Vaguine |
| 4,462,412 A | 7/1984 | Turner |
| 4,572,190 A | 2/1986 | Azam et al. |
| 4,798,215 A | 1/1989 | Turner |
| 5,097,844 A | 3/1992 | Turner |
| 5,417,210 A | 5/1995 | Funda et al. |
| 5,472,441 A | 12/1995 | Edwards et al. |
| 5,800,484 A | 9/1998 | Gough et al. |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Andrew Gilbert

(57) ABSTRACT

Disclosed is a system and method for enabling user preview and control of the size and shape of an electromagnetic energy field used in a surgical procedure. The disclosed system includes a selectively activatable source of microwave surgical energy in the range of about 900 mHz to about 5 gHz in operable communication with a graphical user interface and a database. The database is populated with data corresponding to the various surgical probes, such as microwave ablation antenna probes, that may include a probe identifier, the probe diameter, operational frequency of the probe, ablation length of the probe, ablation diameter of the probe, a temporal coefficient, a shape metric, and the like. The probe data is graphically presented on the graphical user interface where the surgeon may interactively view and select an appropriate surgical probe. Three-dimensional views of the probe(s) may be presented allowing the surgeon to interactively rotate the displayed image.

24 Claims, 9 Drawing Sheets

(56) References Cited

U.S. PATENT DOCUMENTS

| | | | |
|---|---|---|---|
| 5,863,290 | A | 1/1999 | Gough et al. |
| 5,904,709 | A * | 5/1999 | Arndt et al. ............ 607/101 |
| 5,951,547 | A | 9/1999 | Gough et al. |
| 6,031,375 | A | 2/2000 | Atalar et al. |
| 6,073,051 | A | 6/2000 | Sharkey et al. |
| 6,241,725 | B1 | 6/2001 | Cosman |
| 6,245,065 | B1 | 6/2001 | Panescu et al. |
| 6,246,898 | B1 * | 6/2001 | Vesely et al. ............ 600/424 |
| 6,273,886 | B1 | 8/2001 | Edwards et al. |
| 6,350,276 | B1 | 2/2002 | Knowlton |
| 6,358,245 | B1 | 3/2002 | Edwards et al. |
| 6,375,606 | B1 | 4/2002 | Garibaldi et al. |
| 6,451,015 | B1 | 9/2002 | Rittman, III et al. |
| 6,464,689 | B1 | 10/2002 | Qin |
| 6,506,189 | B1 | 1/2003 | Rittman, III et al. |
| 6,551,311 | B2 | 4/2003 | Lee et al. |
| 6,575,969 | B1 * | 6/2003 | Rittman et al. ............ 606/41 |
| 6,603,994 | B2 | 8/2003 | Wallace et al. |
| 6,622,731 | B2 | 9/2003 | Daniel et al. |
| 6,725,080 | B2 | 4/2004 | Melkent et al. |
| 6,783,523 | B2 | 8/2004 | Qin et al. |
| 6,994,704 | B2 | 2/2006 | Qin et al. |
| 7,025,765 | B2 | 4/2006 | Balbierz et al. |
| 7,108,696 | B2 | 9/2006 | Daniel et al. |
| 7,122,031 | B2 | 10/2006 | Edwards et al. |
| 7,160,296 | B2 | 1/2007 | Pearson et al. |
| 7,282,050 | B2 | 10/2007 | Starkebaum et al. |
| 7,344,533 | B2 | 3/2008 | Pearson et al. |
| 7,400,930 | B2 | 7/2008 | Sharkey et al. |
| 7,419,487 | B2 | 9/2008 | Johnson et al. |
| 7,439,736 | B2 | 10/2008 | Meaney et al. |
| 7,467,015 | B2 | 12/2008 | Van der Weide |
| 7,565,207 | B2 | 7/2009 | Turner et al. |
| 2002/0022836 | A1 | 2/2002 | Goble et al. |
| 2003/0097130 | A1 * | 5/2003 | Muller et al. ............ 606/41 |
| 2003/0199755 | A1 * | 10/2003 | Halperin et al. ............ 600/411 |
| 2003/0199863 | A1 | 10/2003 | Swanson et al. |
| 2004/0097805 | A1 | 5/2004 | Verard et al. |
| 2004/0147920 | A1 | 7/2004 | Keidar |
| 2004/0167392 | A1 * | 8/2004 | Halperin et al. ............ 600/411 |
| 2004/0242992 | A1 | 12/2004 | Hareyama |
| 2005/0205566 | A1 | 9/2005 | Kassayan |
| 2005/0228251 | A1 * | 10/2005 | Grabb et al. ............ 600/407 |
| 2006/0106375 | A1 | 5/2006 | Werneth et al. |
| 2006/0289528 | A1 | 12/2006 | Chiu et al. |
| 2007/0066971 | A1 | 3/2007 | Podhajsky |
| 2007/0100405 | A1 | 5/2007 | Thompson et al. |
| 2007/0118101 | A1 | 5/2007 | Mahesh et al. |
| 2007/0124128 | A1 * | 5/2007 | Connacher ............ G06F 3/016 703/11 |
| 2007/0191825 | A1 | 8/2007 | Cronin et al. |
| 2008/0015664 | A1 * | 1/2008 | Podhajsky ............ 607/99 |
| 2008/0183165 | A1 | 7/2008 | Buysse et al. |
| 2008/0319434 | A1 | 12/2008 | Rick et al. |
| 2009/0221999 | A1 * | 9/2009 | Shahidi ............ A61B 18/18 606/33 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 5-123327 A | 5/1993 |
| JP | 06343644 | 12/1994 |
| JP | 7-47079 | 2/1995 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2007-135894 A | 6/2007 |
| JP | 2007-144180 A | 6/2007 |
| JP | 2007-155348 A | 6/2007 |
| JP | 2009-018169 A | 1/2009 |
| SU | 166452 | 11/1964 |
| SU | 401367 | 11/1974 |
| SU | 727201 | 4/1980 |
| WO | WO96/34571 | 11/1996 |
| WO | WO97/41924 | 11/1997 |
| WO | WO97/43971 | 11/1997 |
| WO | WO00/48672 | 8/2000 |
| WO | WO00/51513 | 9/2000 |
| WO | WO00/53113 | 9/2000 |
| WO | WO01/01847 | 1/2001 |
| WO | WO01/74252 | 10/2001 |
| WO | WO02/45790 | 6/2002 |
| WO | WO02/061880 | 8/2002 |

(56) References Cited

FOREIGN PATENT DOCUMENTS

| WO | WO2004/112628 | 12/2004 |
|---|---|---|
| WO | WO2005/016119 | 2/2005 |
| WO | 2007/059172 A2 | 5/2007 |
| WO | 2008/090484 A2 | 7/2008 |
| WO | 2010/064154 A1 | 6/2010 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP 10158944 dated Jun. 21, 2010.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.

(56) References Cited

OTHER PUBLICATIONS

Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedance" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, OApr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.

(56) References Cited

OTHER PUBLICATIONS

Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
S. Humphries Jr. et al., "Finite•Element Codes to Model Electrical Heating and Non•Llnear Thermal Transport in Biological Media", Proc. ASME HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.

(56) References Cited

OTHER PUBLICATIONS

International Search Report PCT/US98/18640 dated Jan. 29, 1998.
International Search Report PCT/US98/23950 dated Jan. 14, 1998.
International Search Report PCT/US99/24869 dated Feb. 11, 2000.
European Search Report for EP10158944 dated Jun. 10, 2010.
Japanese Office Action, and English translation, dated Jul. 10, 2015 from Application No. JP 2014-122359.
Japanese Office Action dated Apr. 7, 2015 from Application No. JP 2014-122359.
Extended European Search Report dated Apr. 14, 2015 from Application No. EP 14196930.3.
Australian Patent Examination Report No. 1 from Appl. No. AU 2014202855 dated Jul. 21, 2015.
Notice of Final Rejection from Japanese Appl. No. 2014-122359 mailed Nov. 2, 2015.

* cited by examiner

MICROWAVE ABLATION SYSTEM WITH USER-CONTROLLED ABLATION SIZE AND METHOD OF USE

BACKGROUND

1. Technical Field

The present disclosure relates to systems and methods for providing energy to biological tissue and, more particularly, to systems and methods for enabling user selection of the size and shape of a microwave energy field used in a surgical procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In tissue ablation electrosurgery, the radio frequency energy may be delivered to targeted tissue by an antenna or probe.

In the case of tissue ablation, a high radio frequency energy in the range of about 300 mHz to about 300 gHz is applied to a targeted tissue site to create an ablation volume, which may have a particular size and shape. The particular type of tissue ablation procedure may dictate a particular ablation volume in order to achieve the desired surgical outcome. By way of example, and without limitation, a spinal ablation procedure may call for a longer, more narrow ablation volume, whereas in a prostate ablation procedure, a more spherical ablation volume may be required.

The ablation volume may be affected by various factors, including without limitation, probe construction, antenna size and shape, frequency, energy level, energy delivery method, and duration of energy delivery. Conventionally, a surgeon must rely upon professional experience and published specifications to select an ablation probe and related electrosurgical parameters with which to achieve a desired ablation volume for a particular patient.

SUMMARY

The present disclosure provides an electromagnetic surgical ablation system having a generator assembly that includes generator module that is configured to provide radiofrequency surgical energy, such as electrosurgical or microwave energy. A processor is included in the generator assembly that is operably coupled to the generator module and a user interface. The user interface may include a graphic touchscreen display, as well as switches and illuminated indicators. The user interface displays a graphical representation of a surgical instrument, such as without limitation a microwave antenna probe. The graphical representation includes an image corresponding to the instrument's radiating field, such as without limitation an antenna probe ablation pattern. The disclosed system includes a database in operable communication with the processor that is adapted to store probe parameters corresponding to at least one antenna probe. A user, typically a surgeon, may then use the user interface to graphically view various probe parameters stored within the database, and thereby choose an appropriate instrument (e.g., ablation probe) with which to perform a surgical procedure. In an embodiment, a shape selection user interface element is provided to receive a shape selection input, which may reflect the surgeon's choice of instrument. In an embodiment, an identifier within the selected probe is recognized by the generator assembly to confirm the actual probe used by the surgeon corresponds to the selected probe.

In some embodiments, a three-dimensional view of a probe and an ablation pattern corresponding thereto is displayed on the user interface. A rotation user interface element may be provided by the user interface, wherein rotation the user interface element is configured to accept an input which causes the user interface to rotate the displayed three dimensional view. In some embodiments, a temporal user interface element is provided by the user interface that is configured to accept a temporal user input which, in response thereto, causes the graphical display to present an animation representative of a change in a probe parameter with respect to time.

Also provided is a method for computer-assisted surgical instrument selection, comprised of providing a selectively-activatable source of electromagnetic surgical energy that includes a user interface, and providing a database in operable communication with the source of electromagnetic energy. The database is populated with at least one surgical instrument parameter and at least one identification parameter associated with a surgical instrument. A visual representation is generated of at least one instrument parameter and displayed on the user interface. At least one associated identification parameter associated with a surgical instrument (e.g., a model number or a clinical designation) may also be displayed. A surgeon responds to the visual display by selecting, with the user interface, a desired surgical instrument. The surgeon activates the source of electromagnetic surgical energy to supply electromagnetic surgical energy to the selected surgical instrument. A surgeon may view a plurality of probe images prior to making a selection.

Also disclosed is a computer-readable medium storing a set of programmable instructions configured for being executed by at least one processor for performing a method for computer-assisted surgical instrument selection as described herein.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
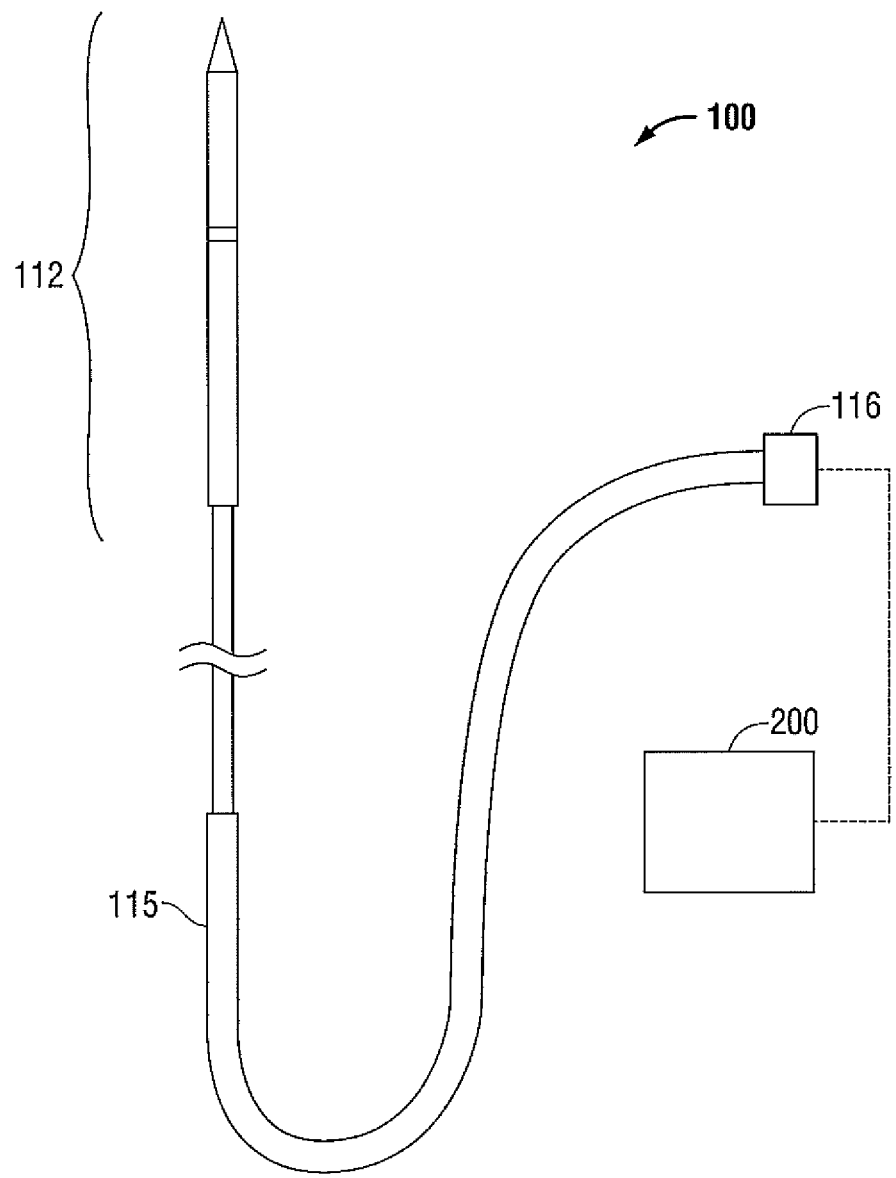
FIG. 1 shows a diagram of a microwave ablation system having a microwave antenna assembly in accordance with the present disclosure.

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed art.

In the drawings and in the descriptions that follow, the term "proximal," as is traditional, shall refer to the end of the instrument that is closer to the user, while the term "distal" shall refer to the end that is farther from the user.

FIG. 1 shows an embodiment of a microwave ablation system 100 in accordance with the present disclosure. The microwave ablation system 100 includes a microwave antenna probe 112 connected by a cable 115 to connector 116, which may further operably connect the antenna probe 112 to a generator assembly 200 configured to provide, e.g., microwave or RF energy in a range of about 915 mHz to about 2450 mHz. Antenna probe 112, as shown, is a dipole microwave antenna assembly, but other antenna assemblies, e.g., choked, wet-tip, monopole or leaky wave antenna assemblies, may also utilize the principles set forth herein.

Figure 2:
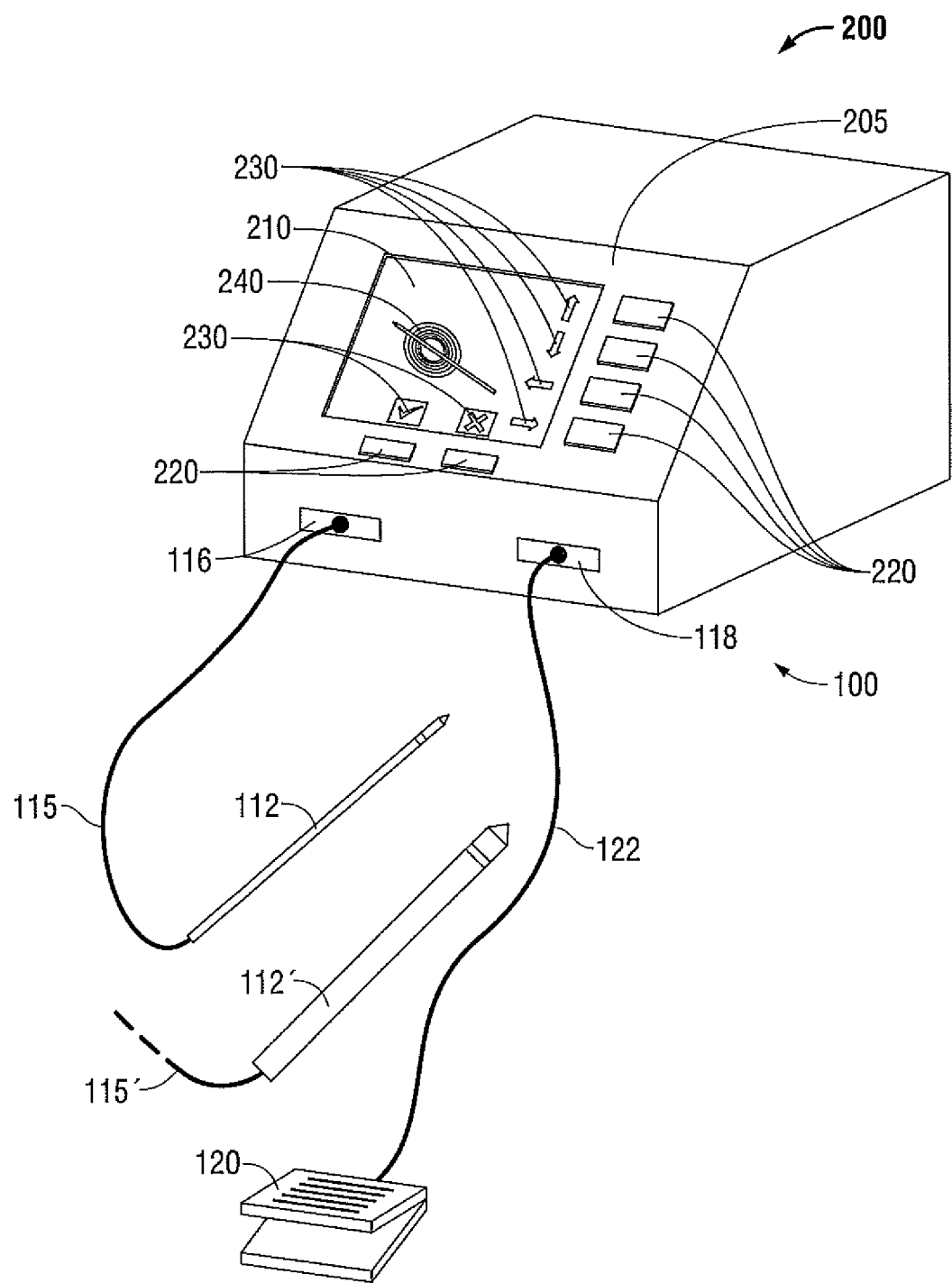
FIG. 2 shows a diagram of a microwave ablation system that includes a user interface for displaying and controlling ablation patterns in accordance with the present disclosure.

In greater detail, FIG. 2 illustrates a microwave ablation system 100 in accordance with the present disclosure. The disclosed system includes an actuator 120, which may be a footswitch, a handswitch, a bite-activated switch, or any other suitable actuator. Actuator 120 is operably coupled by a cable 122 via connector 118 to generator assembly 200. Cable 122 may include one or more electrical conductors for conveying an actuation signal from actuator 120 to generator assembly 200. In an embodiment, actuator 120 is operably coupled to generator assembly 200 by a wireless link, such as without limitation, a radiofrequency or infrared link. At least one additional or alternative microwave antenna probe 112' may be included with microwave ablation system 100 that may have characteristics distinct from that of microwave antenna probe 112. For example without limitation, microwave antenna probe 112 may be a 12 gauge probe suitable for use with energy of about 915 mHz, while microwave antenna probe 112' may be a 14 gauge probe suitable for use with energy of about 915 mHz. Other probe variations are contemplated within the scope of the present disclosure, for example without limitation, a 12 gauge operable at 2450 mHz, and a 14 gauge operable at 2450 mHz. In use, the user typically a surgeon, may interact with user interface 205 to preview operational characteristics of available probes 112, 112' et seq., and to choose a probe for use in accordance with surgical requirements.

Generator assembly 200 includes a generator module 286 in operable communication with processor 282 that is configured as a source of RF and/or microwave energy. In an embodiment, generator module 286 is configured to provide energy of about 915 mHz. Generator module 286 may also be configured to provide energy of about 2450 mHz (2.45 gHz.) The present disclosure contemplates embodiments wherein generator module 286 is configure to generate a frequency other than about 915 mHz or about 2450 mHz, and embodiments wherein generator module is configured to generate variable frequency energy. Probe 112 is operably coupled to an energy output of generator module 286.

Actuator 120 is operably coupled to processor 282 via user interface 210. In embodiments, actuator 120 may be operably coupled to processor, and/or to generator 286 by a cable connection, or a wireless connection.

Generator assembly 200 also includes user interface 205, that may include a display 210 such as, without limitation, a flat panel graphic LCD display, adapted to visually display at least one user interface element 230, 240. In an embodiment, display 210 includes touchscreen capability (not explicitly shown), e.g., the ability to receive input from an object in physical contact with the display, such as without limitation a stylus or a user's fingertip, as will be familiar to the skilled practitioner. A user interface element 230, 240 may have a corresponding active region, such that, by touching the screen within the active region associated with the user interface element, an input associated with the user interface element is received by the user interface 205.

User interface 205 may additionally or alternatively include one or more controls 220, that may include without limitation a switch (e.g., pushbutton switch, toggle switch, slide switch) and/or a continuous actuator (e.g., rotary or linear potentiometer, rotary or linear encoder.) In an embodiment, a control 220 has a dedicated function, e.g., display contrast, power on/off, and the like. Control 220 may also have a function which may vary in accordance with an operational mode of the ablation system 100. A user interface element 230 may be positioned substantially adjacently to control 220 to indicate the function thereof. Control 220 may also include an indicator, such as an illuminated indicator (e.g., a single- or variably-colored LED indicator.)

Figure 3:
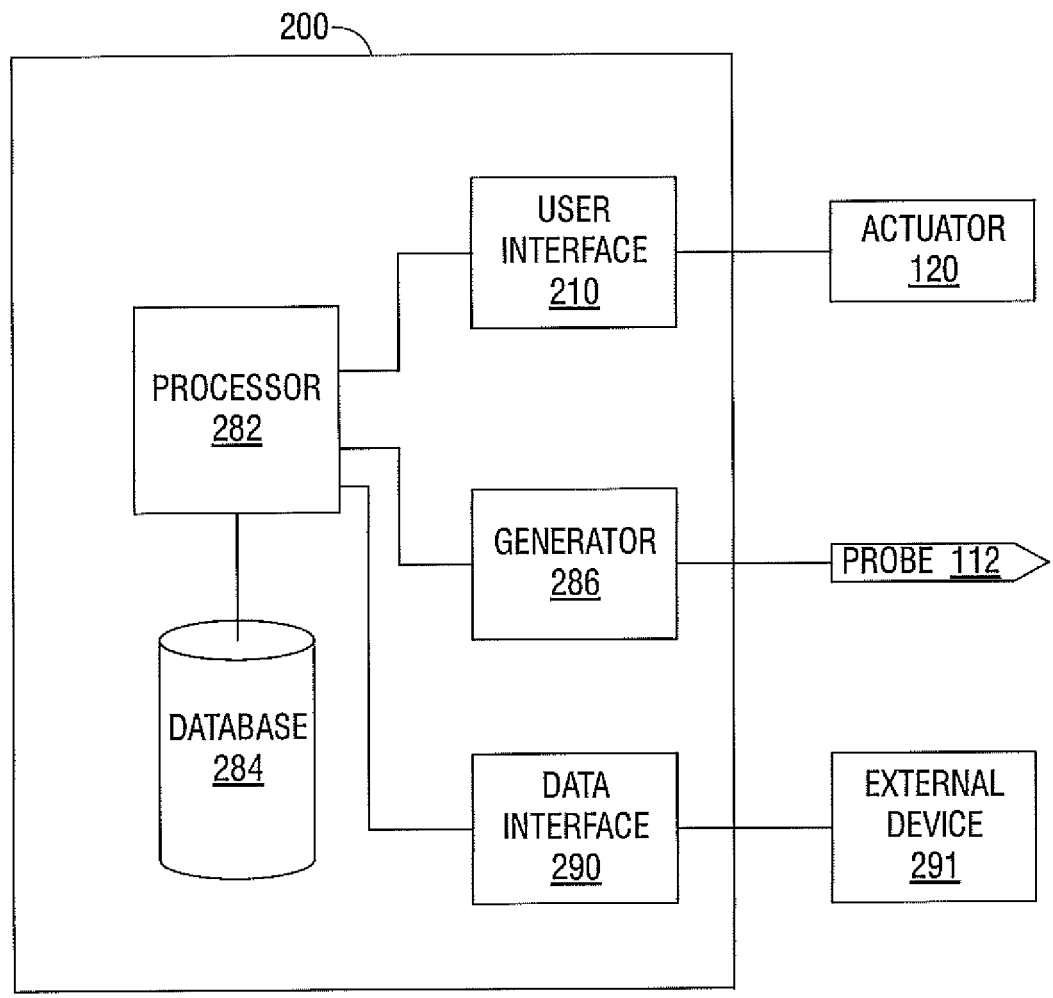
FIG. 3 is a block diagram of a microwave ablation system in accordance with the present disclosure.

Turning now to FIG. 3, generator assembly 200 includes a processor 282 that is operably coupled to user interface 210. A storage device 288 is operably coupled to processor 282, and may include random-access memory (RAM), read-only memory (ROM), and/or non-volatile memory (NV-RAM, Flash, and disc-based storage.) Storage device 288 may include a set of program instructions executable on processor 282 for executing a method for displaying and controlling ablation patterns in accordance with the present disclosure. Generator assembly 200 may include a data interface 290 that is configure to provide a communications link to an external device 291. In an embodiment, data interface 290 may be any of a USB interface, a memory card slot (e.g., SD slot), and/or a network interface (e.g., 100 BaseT Ethernet interface or an 802.11 "WiFi" interface.) External device 291 may be any of a USB device (e.g., a memory stick), a memory card (e.g., an SD card), and/or a network-connected device (e.g., computer or server.) Generator assembly 200 may also include a database 284 that is configured to store and retrieve probe data, e.g., parameters associated with one or more probes 112. Parameters stored in database 284 in connection with a probe may include, but are not limited to, probe identifier, a probe diameter, a frequency, an ablation length, an ablation diameter, a temporal coefficient, a shape metric, and/or a frequency metric. In an embodiment, ablation pattern topology may be included in database 284, e.g., a wireframe model of a probe 112 and/or an ablation pattern associated therewith.

Database 284 may also be maintained at least in part by data provided by external device 291 via data interface 290. For example without limitation, probe data may be uploaded from an external device 291 to database 284 via data interface 290. Additionally or alternatively, probe data may be manipulated, e.g., added, modified, or deleted, in accordance with data and/or instructions stored on external device 291. In an embodiment, the set of probe data represented in database 284 is automatically synchronized with corresponding data contained in external device 291 in response to external device 291 being coupled (e.g., physical coupling and/or logical coupling) to data interface 290.

Processor 282 is programmed to enable a user, via user interface 205 and/or display 210, to view at least one ablation pattern and/or other probe data corresponding to a probe 112 et seq. For example, a surgeon may determine that a substantially spherical ablation pattern is necessary. The surgeon may activate a "select ablation shape" mode of operation for generator assembly 200, preview a number of probes by reviewing graphically and textually presented data on display 210, optionally or alternatively manipulate a graphic image by, for example, rotating the image, and to select an appropriate probe 112 et seq. based upon displayed parameters. The selected probe may then be coupled to generator assembly 200 for use therewith. In an embodiment, probe 112 may include an identifier (not explicitly shown) that provides an identification signal to generator assembly 200 to facilitate confirmation that a particular probe 112 of the selected type is coupled to generator assembly 200.

In an embodiment, a surgeon may input via user interface 205 a probe parameter to cause generator assembly 200 to present at least one probe corresponding thereto. For example, a surgeon may require a 3.0 cm diameter ablation pattern, and provide an input corresponding thereto. In response, the generator assembly 200 may preview a corresponding subset of available probes that match or correlate to the inputted parameter.

Figure 4A:
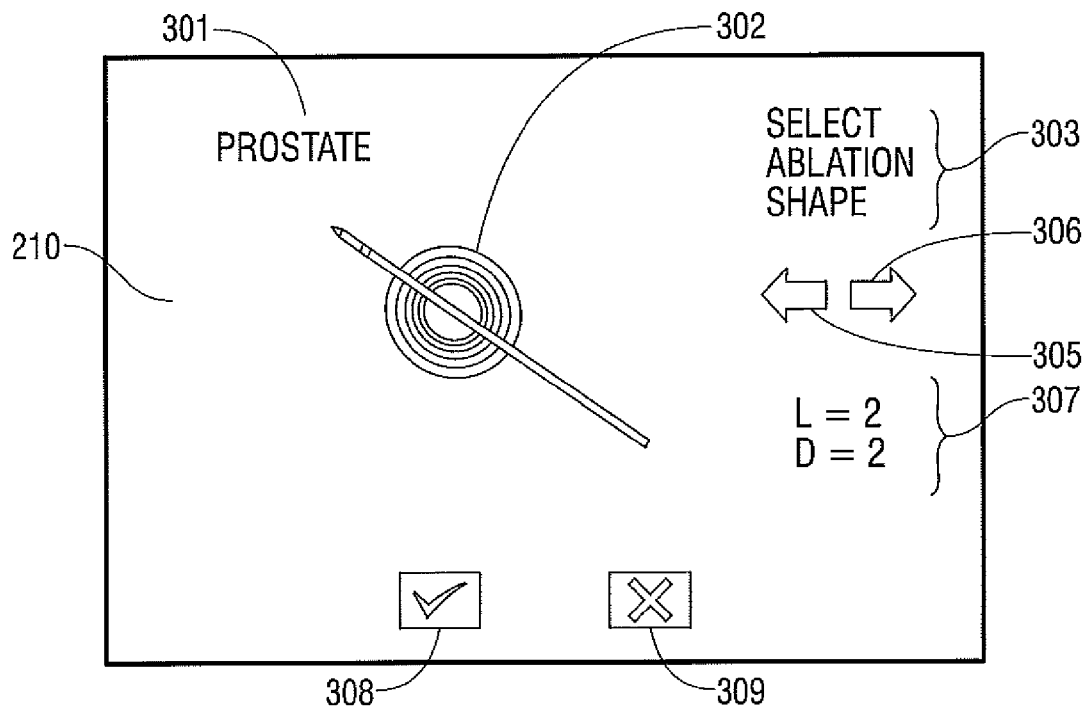
FIG. 4A shows a user interface in accordance with the present disclosure wherein a side view of a first ablation pattern is displayed.

Turning now to FIGS. 4A-4D, generator assembly 200 provides a user interface 210 which may present a probe image 302. Probe image 302 may be a three dimensional (e.g., 3D) graphic rendering of the characteristics of probe 112 that are stored in database 284. Probe image 302 may be rendered using any suitable rendering technique, such as wire-frame projections and/or ray-tracing. User interface 210 provides a select ablation shape indicator 303, which may be a graphic icon or a textual command, that informs the user that generator assembly 200 is in a probe selection mode (e.g., probe select and/or ablation shape selection mode). A shape selection user interface element 305, 306 may be provided for receiving a shape selection user input thereby enabling a user to choose an ablation shape from among one of a set of ablation shapes and/or probes stored in database 282. A probe designation 301 (e.g., probe name) may be displayed. As seen in FIG. 4A, a shape selection user interface element 305, 306 may include a graphic icon, such as without limitation, an arrowhead, and/or may include textual commands, such as "previous" or "next."

Additional parameters 307 of one or more displayed probes 112 may be presented on display 210, which may include probe diameter, frequency, ablation length, ablation diameter, and/or shape metric. A shape metric is defined as a minimum ablation diameter expressed as a percentage of a maximum ablation diameter, e.g., $100(d_{min}/d_{max})$, where $d_{min}$ is a minimum ablation diameter and $d_{max}$ is a maximum ablation diameter.

Figure 4B:
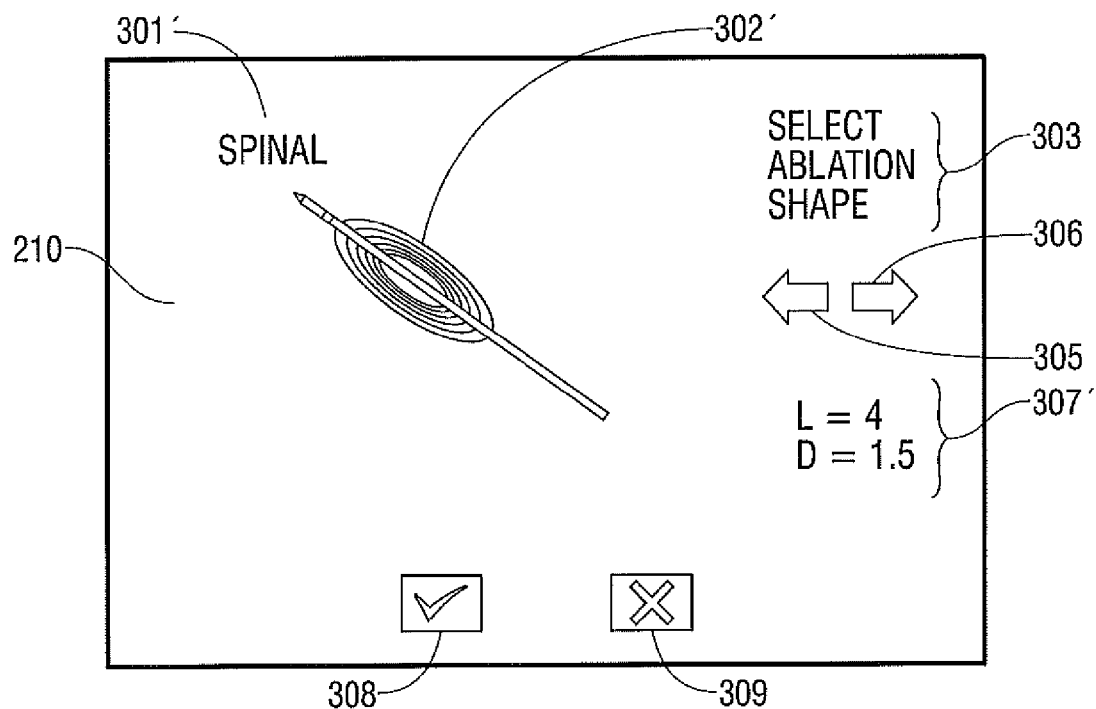
FIG. 4B shows a user interface in accordance with the present disclosure wherein a side view of a second ablation pattern is displayed.

By actuating a shape selection icon, a user may cause display 210 to depict characteristics of a different probe 112 as stored in database 282. For example, as shown in FIG. 4B, a user has made a shape selection by activating a shape selection user interface element 305, 306, causing an characteristics of an alternative probe 302' to be displayed. The corresponding user interface elements are updated accordingly, such that, as seen in FIG. 4B, the corresponding probe designation 301', probe image 302'; and additional parameters 307' correctly reflect characteristics of the currently-displayed probe.

Figure 4C:
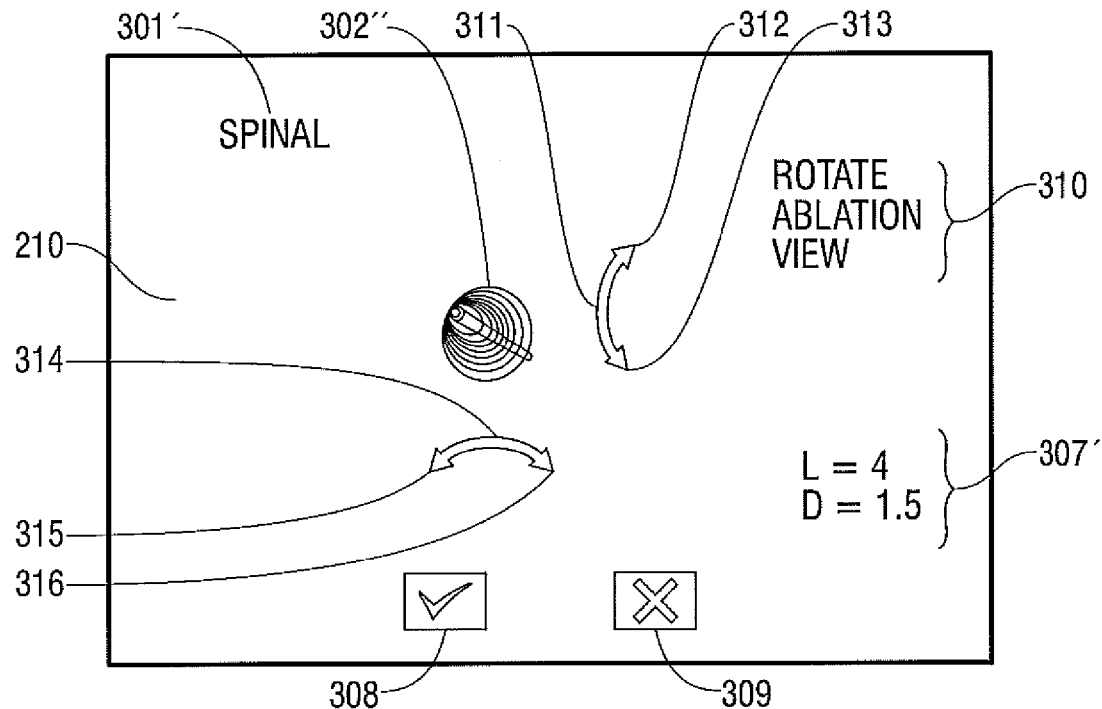
FIG. 4C shows a user interface in accordance with the present disclosure wherein an oblique view of a second ablation pattern is displayed.
Figure 4D:
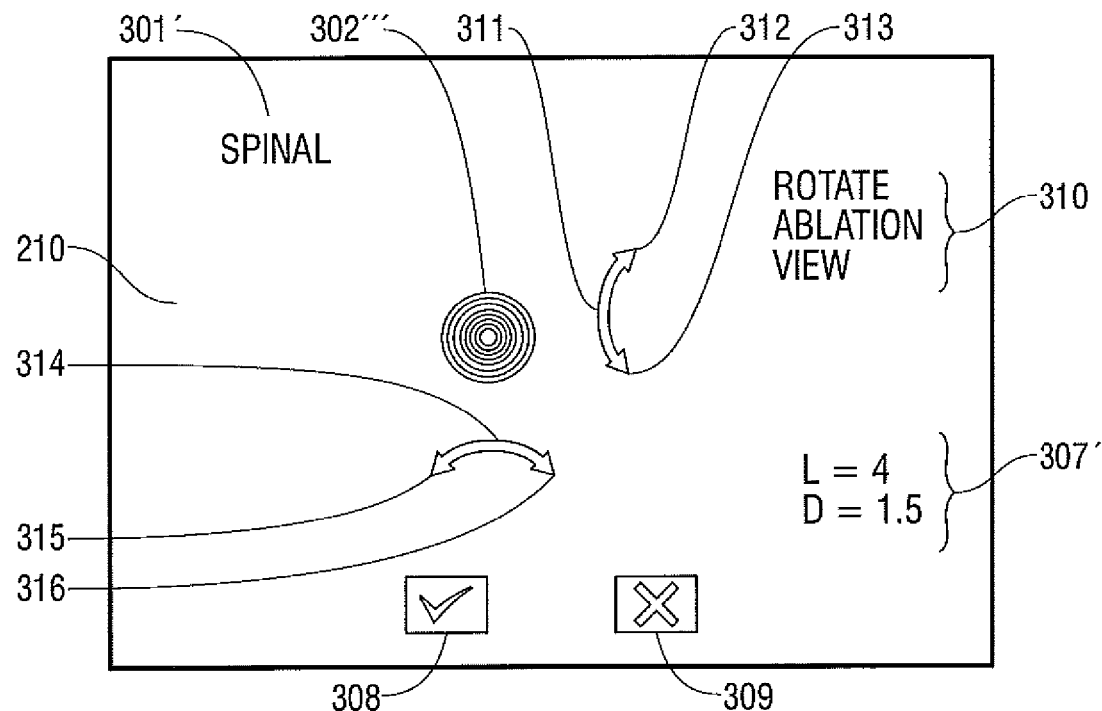
FIG. 4D shows a user interface in accordance with the present disclosure wherein an axial view of a second ablation pattern is displayed.

As shown in FIGS. 4C and 4D, the user may activate a rotate ablation image mode of display for generator assembly 200 wherein a rotation user interface element 312, 314 may be used to display alternate probe image views 302", 302"' in response to receiving a rotation user input. In an embodiment, rotation user interface element 312, 314 may be a hidden and/or invisible region of display 210, permitting the user to cause the probe image 302' to be rotated by, for example, wiping a fingertip on the display 210 (e.g., gesturing) to indicate the direction and axis of rotation. Rotation user interface element 312, 314 may be visible and include arrowheads 311, 313, 315, 316 to denote upward rotation, downward rotation, left rotation, and right rotation, respectively, of probe image 302'.

In an embodiment, at least one patient image, e.g., ultrasound, CT scan, MRI, and the like, (not explicitly shown) may be presented on display 210 over which a displayed probe 302 is superimposed thereupon to enable the user to visualize an ablation pattern of a probe 302 in situ with surrounding tissue. The patient image may be a 3D image and responsive to an input received by rotation user interface element 312, 314, such that the patient image and displayed probe 302 rotate together in a substantially synchronized manner to enable a user to visualize the relationship of the probe 302, ablation pattern thereof and surrounding tissue from a plurality of viewing angles.

A temporal user interface element (not explicitly shown) may be provided to enable a user to view changes in an ablation pattern over time. Temporal user interface element may include, for example, a slider, which may be positioned at a desired point along a time scale to view an ablation pattern corresponding thereto. In an embodiment, actuation of a temporal user interface element may cause an animated depiction of an ablation pattern to be displayed. Such animation may be displayed in real-time, slower than real-time, or faster than real-time.

A user may confirm a probe choice by activating an accept selection user interface element 308, or exit a probe selection mode without making a selection by activating a cancel selection user interface element 309.

Figure 5A:
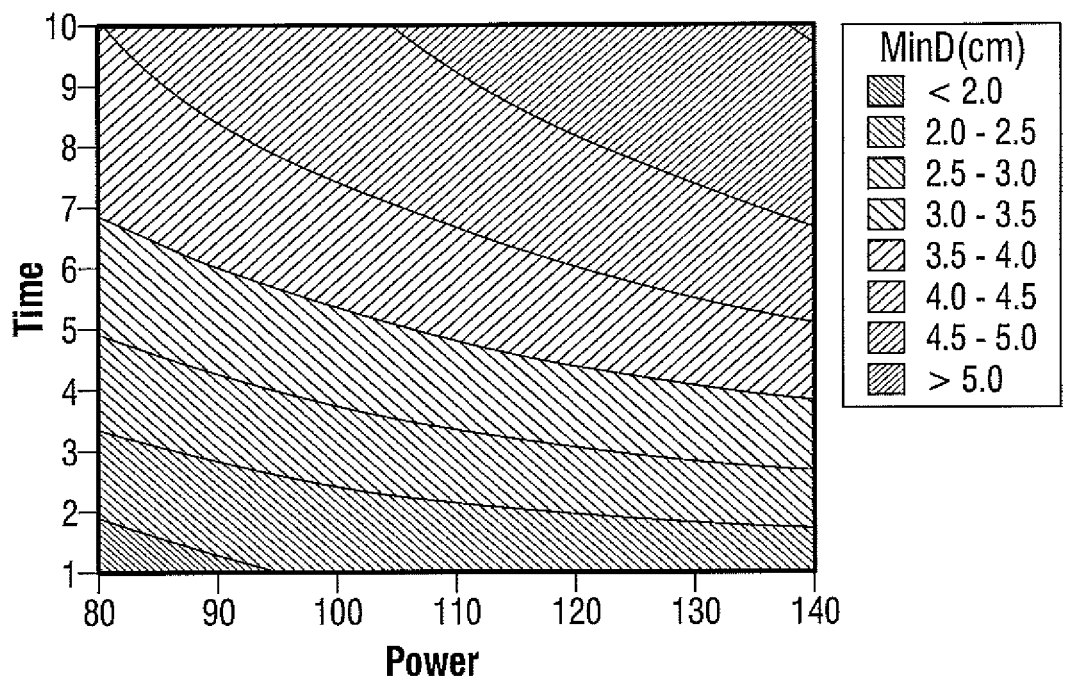
FIG. 5A is a graph in accordance with the present disclosure illustrating a relationship between an ablation diameter, time, and power with respect to a 12 gauge, 915 mHz choked wet tip dipole ablation probe.
Figure 5B:
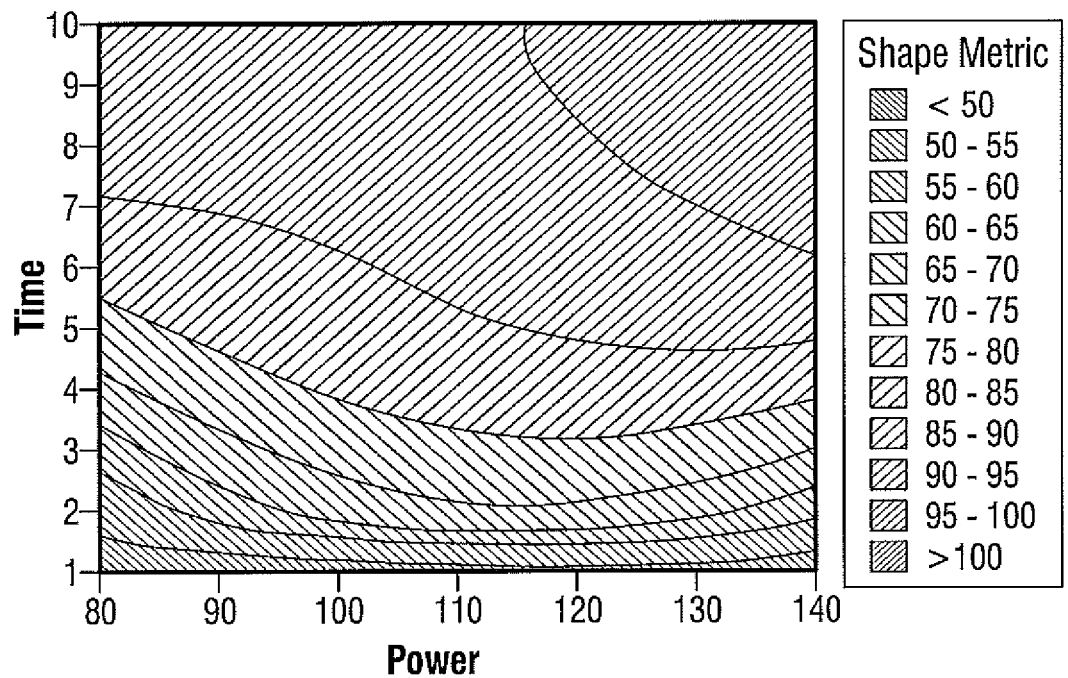
FIG. 5B is a graph in accordance with the present disclosure illustrating a relationship between an ablation shape, time, and power with respect to a 12 gauge, 915 mHz choked wet tip dipole ablation probe.
Figure 6A:
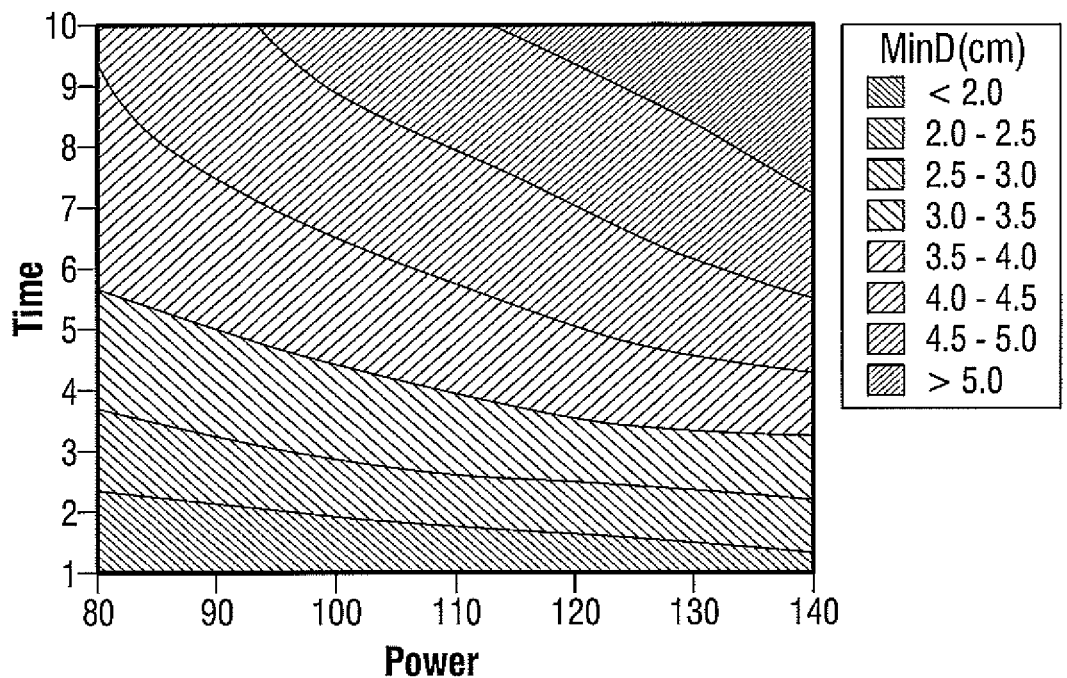
FIG. 6A is a graph in accordance with the present disclosure illustrating a relationship between an ablation diameter, time, and power with respect to a 12 gauge, 2450 mHz choked wet tip dipole ablation probe.
Figure 6B:
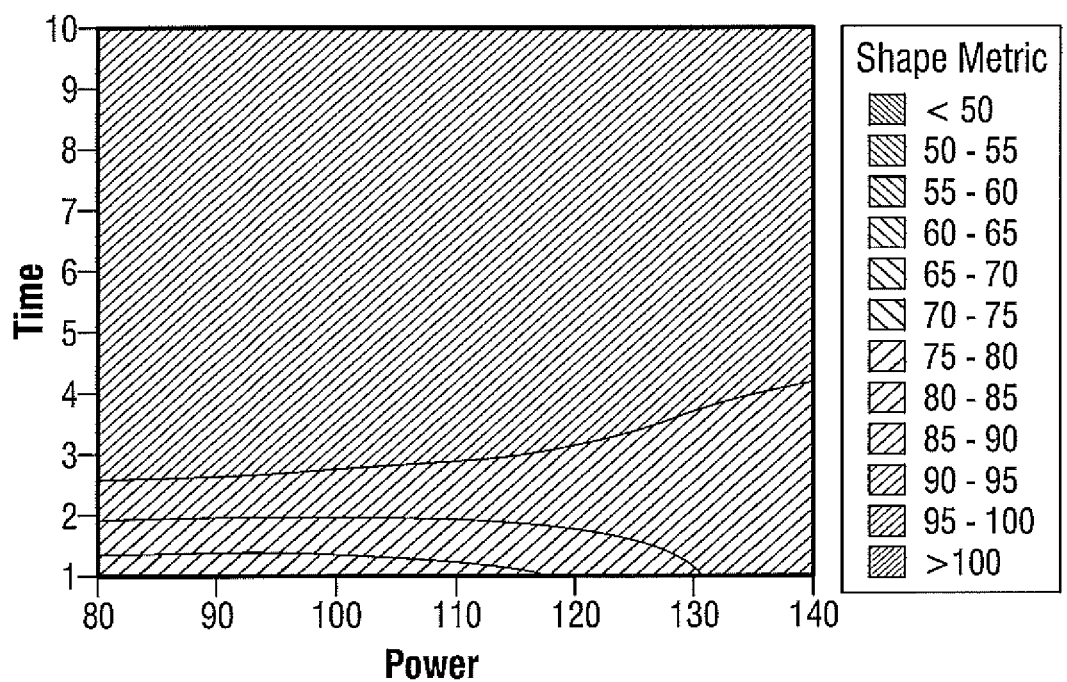
FIG. 6B is a graph in accordance with the present disclosure illustrating a relationship between an ablation shape, time, and power with respect to a 12 gauge, 2450 mHz choked wet tip dipole ablation probe.
Figure 7A:
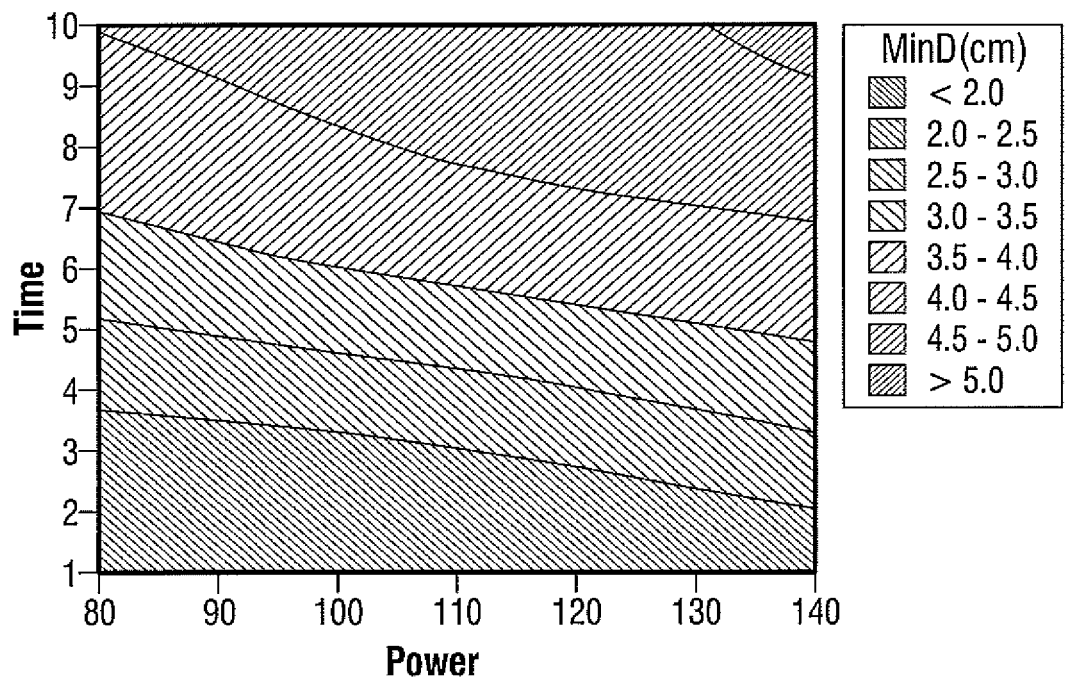
FIG. 7A is a graph in accordance with the present disclosure illustrating a relationship between an ablation diameter, time, and power with respect to a 14 gauge, 915 mHz choked wet tip dipole ablation probe.
Figure 7B:
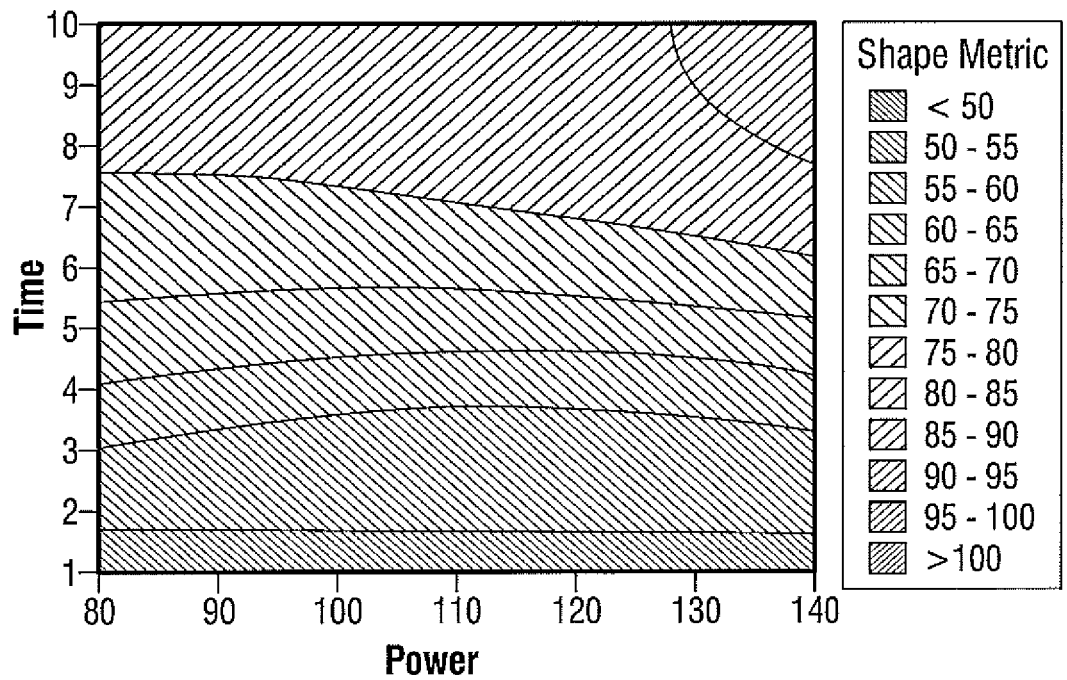
FIG. 7B is a graph in accordance with the present disclosure illustrating a relationship between an ablation shape, time, and power with respect to a 14 gauge, 915 mHz choked wet tip dipole ablation probe.
Figure 8A:
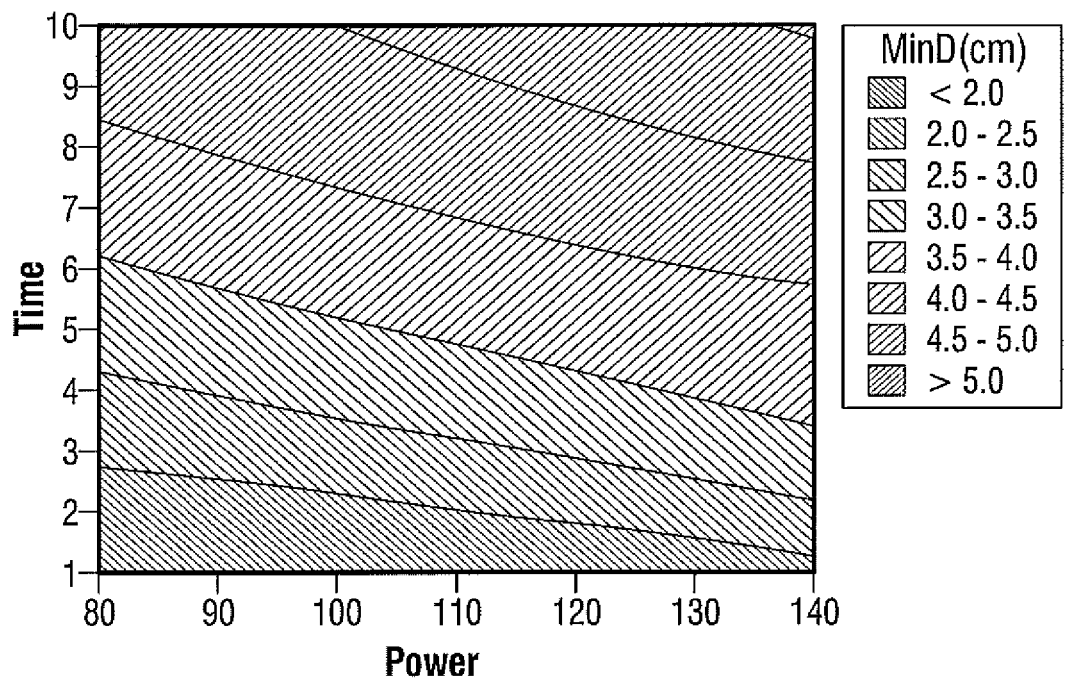
FIG. 8A is a graph in accordance with the present disclosure illustrating a relationship between an ablation diameter, time, and power with respect to a 14 gauge, 2450 mHz choked wet tip dipole ablation probe.
Figure 8B:
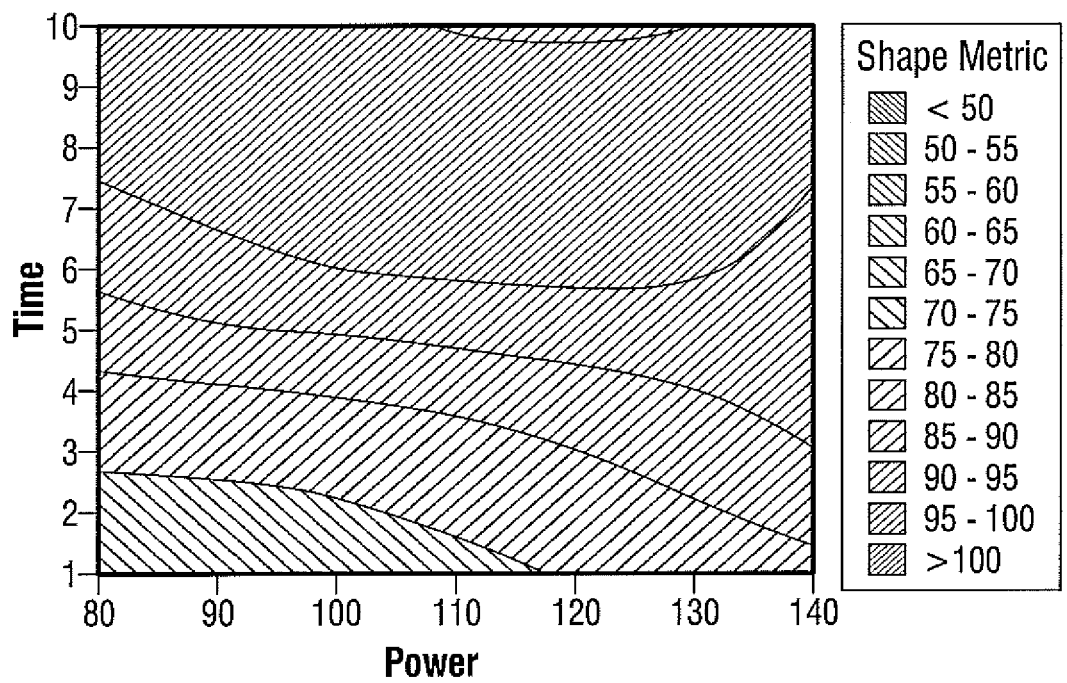
FIG. 8B is a graph in accordance with the present disclosure illustrating a relationship between an ablation shape, time, and power with respect to a 14 gauge, 2450 mHz choked wet tip dipole ablation probe.

Turning now to FIGS. 5A, 5B, 6A, 6C, 7A, 7D, 8A, and 8B, examples of measures minimum ablation diameter and shape metric are shown with respect to probe diameter and operating frequency. FIG. 5A illustrates a relationship between an ablation diameter, time, and power of a 12 gauge diameter; 915 mHz choked wet tip dipole ablation probe. FIG. 5B is a graph illustrating a relationship between an ablation shape, time, and power of a 12 gauge, 915 mHz choked wet tip dipole ablation probe. FIG. 6A illustrates a relationship between an ablation diameter, time, and power of a 12 gauge diameter, 2450 mHz choked wet tip dipole ablation probe. FIG. 6B is a graph illustrating a relationship between an ablation shape, time, and power of a 12 gauge, 2450 mHz choked wet tip dipole ablation probe. FIG. 7A illustrates a relationship between an ablation diameter, time, and power with respect to a 14 gauge, 915 mHz choked wet tip dipole ablation probe. FIG. 7B is a graph illustrating a relationship between an ablation shape, time, and power with respect to a 14 gauge, 915 mHz choked wet tip dipole ablation probe. FIG. 8A depicts a relationship between an ablation diameter, time, and power with respect to a 14 gauge, 2450 mHz choked wet tip dipole ablation probe. FIG. 8B shows a relationship between an ablation shape, time, and power with respect to a 14 gauge, 2450 mHz choked wet tip dipole ablation probe.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electromagnetic surgical ablation system, comprising:
   a generator module configured to provide radiofrequency surgical energy;
   a processor operably coupled to the generator module and programmed to respond to a shape selection user input corresponding to an antenna probe ablation pattern, wherein the processor causes a probe image corresponding to the antenna probe ablation pattern to be transmitted to a user interface operably coupled to the processor, the user interface is configured to:
      display a probe image received from the processor;
      receive the shape selection user input corresponding to an antenna probe ablation pattern; and
      display a rotated view of the antenna probe ablation pattern in response to rotational input;
   a database in operable communication with the processor and adapted to store a wireframe model corresponding to at least one antenna probe ablation pattern; and
   a temporal user interface element configured to display on the user interface an animated depiction over a time scale of the antenna probe ablation pattern.

2. The electromagnetic surgical ablation system in accordance with claim 1, wherein the user interface is configured to display an identifier corresponding to one of said at least one antenna probe selected according to the shape selection user input.

3. The electromagnetic surgical ablation system in accordance with claim 1, wherein the displayed probe image includes a three dimensional rendering of a corresponding probe ablation pattern.

4. The electromagnetic surgical ablation system in accordance with claim 1, wherein the user interface is configured to receive rotational input.

5. The electromagnetic surgical ablation system in accordance with claim 1, wherein the user interface is configured to display at least one probe parameter.

6. The electromagnetic surgical ablation system in accordance with claim 5, wherein said at least one probe parameter is selected from the group consisting of a probe identifier, a probe diameter, a frequency, an ablation length, an ablation diameter, and a shape metric.

7. The electromagnetic surgical ablation system in accordance with claim 1, wherein the user interface is configured to receive at least one temporal user input.

8. The electromagnetic surgical ablation system in accordance with claim 7, wherein in response to said at least one temporal user input, the user interface is configured to display a change in an ablation pattern with respect to time.

9. The electromagnetic surgical ablation system in accordance with claim 1, further comprising:
   a data interface operable coupled to the database, wherein the data interface is configured to accept data from at least one external device.

10. The electromagnetic surgical ablation system in accordance with claim 9, wherein the database is modified in accordance with data in said at least one external device.

11. The electromagnetic surgical ablation system in accordance with claim 1, wherein the radiofrequency surgical energy has a frequency selected from the group consisting of about 915 megahertz, and about 2,450 megahertz.

12. The electromagnetic surgical ablation system in accordance with claim 1, wherein the temporal user interface element further includes:
   a slider selectively positionable along a time scale to enable viewing of the ablation pattern corresponding to the desired point along the time scale.

13. The electromagnetic surgical ablation system in accordance with claim 1, wherein the animated depiction of the antenna probe ablation pattern may be displayed in at least one of real-time, slower than real-time, and faster than real-time.

14. A method for computer-assisted surgical instrument selection, comprising the steps of:
   providing the electromagnetic surgical ablation system of claim 1;
   providing the database with at least one instrument parameter and at least one identification parameter associated with a surgical instrument;
   rendering a visual representation of the at least one instrument parameter for display on the user interface;
   displaying with the user interface the visual representation and at least one identification parameter associated with a surgical instrument;
   responding to the visual representation by selecting, with the user interface, a surgical instrument; and
   activating the source of electromagnetic surgical energy to supply electromagnetic surgical energy to the selected surgical instrument.

15. A method in accordance with claim 14, wherein the visual representation is selected from the group consisting of a graphical rendering of an ablation pattern, a graphical rendering of a surgical instrument, a patient image, and an alphanumeric display.

16. A method in accordance with claim 14, wherein one of the at least one instrument parameter is selected from the group consisting of a probe identifier, a probe diameter, a frequency, an ablation length, an ablation diameter, and a shape metric.

17. A method in accordance with claim 14, wherein the visual representation includes a view selected from the group consisting of a three-dimensional view of the at least one instrument parameter, and a three-dimensional view of a patient image.

18. A method in accordance with claim 17, further comprising:
   providing a rotational interface on the user interface; and
   responding to an actuation of the rotational interface by rotating the three dimensional view.

19. A method in accordance with claim 14, further comprising:
   receiving a first user input indicative of a surgical parameter relating to a surgical procedure; and
   identifying at least one surgical instrument in accordance with the surgical parameter.

20. A method in accordance with claim 11, further comprising:
   providing a temporal user interface element on the user interface; and
   responding to an actuation of the temporal user interface element by animating a three dimensional view of the at least one surgical parameter in accordance with a temporal parameter.

21. A computer-readable medium storing a set of programmable instructions configured for being executed by at least one processor for performing a method for computer-assisted surgical instrument selection, comprising the steps of:
   providing the electromagnetic surgical ablation system of claim 1;
   providing the database with at least one instrument parameter and at least one identification parameter associated with a surgical instrument;
   rendering a visual representation of the at least one instrument parameter for display on the user interface;
   displaying with the user interface the visual representation and at least one identification parameter associated with a surgical instrument;
   responding to the visual representation by selecting, with the user interface, a surgical instrument; and
   activating the source of electromagnetic surgical energy to supply electromagnetic surgical energy to the selected surgical instrument.

22. An electromagnetic surgical ablation system, comprising:
   a generator module configured to provide radiofrequency surgical energy;
   a processor operably coupled to the generator module;
   a database in operable communication with the processor and adapted to store probe parameters corresponding to respective ones of a plurality of antenna probes, wherein the probe parameters include ablation pattern topology including a wireframe model of the antenna probe and an ablation pattern associated therewith; and
   a user interface operably coupled to the processor configured to:
      display a probe image of an antenna probe including an antenna probe ablation pattern; and
      receive a shape selection user input, wherein a user is able to use the user interface to graphically view various ablation pattern topologies stored within the database, and thereby choose an appropriate antenna probe with which to perform a surgical procedure; and
      display a rotated view of the antenna probe ablation pattern in response to rotational input;
   a temporal user interface element configured to display on the user interface an animated depiction over a time scale of an ablation pattern topologies stored within the database.

23. The electromagnetic surgical ablation system in accordance with claim 22, wherein the temporal user interface element further includes:
   a slider selectively positionable along a time scale to enable viewing of the ablation pattern corresponding to the desired point along the time scale.

24. The electromagnetic surgical ablation system in accordance with claim 22, wherein the animated depiction of the antenna probe ablation pattern may be displayed in at least one of real-time, slower than real-time, and faster than real-time.

* * * * *